United States Patent [19]

Kapil et al.

[11] Patent Number: 5,439,891
[45] Date of Patent: Aug. 8, 1995

[54] PROCESS FOR PREPARATION OF PHARMACEUTICAL COMPOSITION WITH ENHANCED ACTIVITY FOR TREATMENT OF TUBERCULOSIS AND LEPROSY

[76] Inventors: Randhir S. Kapil; Usha Zutshi; Kasturi L. Bedi; Gurbax Singh; Ramesh K. Johri; Santosh K. Dhar; Jawahar L. Kaul; Subhash C. Sharma; Gurcharan S. Pahwa; Naveen Kapoor; Ashok K. Tickoo; Manoj K. Tickoo; Uma Kaul; Surjeet Singh; Ram K. Zutshi; Rajinder Singh, all of Regional Research Laboratory, Jammu 180001, India

[21] Appl. No.: 142,973

[22] Filed: Oct. 29, 1993

[51] Int. Cl.⁶ .................. A01N 43/04; A01N 43/30; A01N 43/40; A61K 31/495
[52] U.S. Cl. ........................ 514/31; 514/255; 514/315; 514/464; 514/657; 514/724; 514/924
[58] Field of Search ............... 514/31, 255, 315, 464, 514/657, 724, 924

[56] References Cited

PUBLICATIONS

Johri et al, "An Ayurvedic Formulation 'Trikatu' and its Constituents", J. Ethnopharmacology (Ireland) 1992, vol. 37, No. 2, pp. 85–91).

Annamalai et al, "Effects of 'Trikatu' and Its Individual Components and Piperine on Gastro–Intestinal Tracts: Trikatue-A Bioavailable Enhancer" Indian Drugs (India), 1990, vol. 27, No. 12, pp. 595–604.

Atal et al "Scientific Evidence on the Role of Ayurvedic Herbals on Bio Availability of Drugs", J. Ethnopharmacol, vol. 4, No. 2, pp. 229–232, 1981.

"Influence of Piperine on Rifampicin Blood Levels in Patients of Pulmonary Tuberculosis," J. Assoc. Physicians India, Mar. '85, Issn 000414 5772, vol. 33, No. 3, pp. 223–224 (Abstract).

Primary Examiner—Nathan M. Nutter
Attorney, Agent, or Firm—Michael D. Bednarek; Marks & Murase

[57] ABSTRACT

A new pharmaceutical composition for the treatment of tuberculosis and leprosy, said composition comprising piperine in combination with known antituberculosis or antileprosy drugs or the mixtures thereof.

4 Claims, 12 Drawing Sheets

PROCESS FOR PREPARATION OF PHARMACEUTICAL COMPOSITION WITH ENHANCED ACTIVITY FOR TREATMENT OF TUBERCULOSIS AND LEPROSY

The present invention relates to an new pharmaceutical composition for the treatment of tuberculosis and leprosy. The new composition has increased therapeutic efficacy. The invention particularly relates to a pharmaceutical composition containing piperine anti-tuberculosis/leprotic drugs.

The global problems of combating tuberculosis intensified by the country's economic problem and corresponding lack of health education which makes spitting a national pass-time and covering one's mouth, while coughing, a rare phenomenon.

As tuberculosis is one of the oldest diseases known to man, it has also been one of the hardest to conquer. Till today, it remains one of the six targeted diseases by WHO's expanded programme on immunization. Central Bureau of Health Information figures show rise in number of cases from 610,531 in 1977 to 852,334 in 1987. WHO surveys, however, reveal that each year almost three million people die from tuberculosis 11 over the world. Four to five million new cases of acute, highly contagious pulmonary tuberculosis emerge annually. In addition to this an equal number of less serious forms appear bringing the world total to 10 million new cases every year.

Of this, an estimated two million are children below the age of five.

Though so called wonder drugs are available in the market for the treatment of Tuberculosis and Leprosy they are within the reach of only the affluent. Exact economic impact is difficult to calculate, but the above mentioned facts give a fair idea of the magnitude. Until short course chemotherapy becomes a norm total tuberculosis control will be slow in coming years. Not only does it reduce the default risk but it has cure rate of almost 100% against 70% in long term therapy. The prohibitive factor is, of course, the cost. Rifampicin, even in the west, is the costliest of the tuberculosis drugs. Low requirement of rifampicin and other antituberculsois drugs with enhanced activity combined with shorts course regimen may be the answer to meet the situation.

The quest for newer drugs, dosage forms or better formulations is motivated by an overriding requirement, e.g. minimum possible dose, in a dosage form that will provide controlled, reproducible therapeutic amounts of the drug to the body. The bioavailability is, therefore, an essential part of the drug formulation and has come to be increasingly accepted. In other words it means that performance of the drug in vivo is the most important factor in order to evaluate its efficacy.

A look into the Indian system of the medicine will show that generally complex formulations are prescribed for almost all the ailments. For this matter certain herbs, either in groups or individually, occupy a very prestigious position in the majority of these prescriptions. Some of these groups are:

TRIKATU: *Piper nigrum, Piper longum* & *Zingiber officinalis* in equal proportion W/W.

PANCKOL: *Piper longum* (roots), *Piper longum* (fruits), *Piper Chaba* (roots), *Plumbago zeylanica*.

UMBELLIFEREAE—Herbs: *Carum carvi, Anethum graveolans, Anethum Sowa*.

As examples of the individual herbs *Acorus calamus* (Arcidate) and *Semicarpus anacardium* (Anacardiaceae) have been reported frequently in large number of Ayurvedic formulations. Powdered herbs are combined with other ingredients of the formulations to increase their potency and therapeutic efficacy.

Out of the all the herbs mentioned above TRIKATU or its individual constituents especially *Piper nigrum* and *Piper longum* are the most widely used herbs in Ayurveda. The literature pertaining to the use of these herbs dates back to the period between 6th century Ad and 3rd century BC (Charaka, et al, Charak Samhita, 3rd edn, Nirnaya Sagar Press Bombay, 1941 (in Sanskrit), Kaviraj, K. B., Sushruta Samhita, 2nd ed., Chowkhamba Sanskrit Series, vol. 3, Varanasi, India 1953; Vagbmat, Ashtang Hridaya, Chowkhamba Sanskrit Series, Varanasi, India, 1962 (in Sanskrit). Hand Book of Domestic Medicine and Common Ayurvedic Remedies (1979) published by Central Council of Research in Indian Medicine and Homeopathy, New Delhi in India reveals that out of 370 compound formulations listed therein, 210 contain either Trikatu or its individual ingredients. If the claim made about the individual members of the Trikatu group are examined in literature, it is amazing to find that the single entity have been shown to be panacea for numerous ailments. One, therefore, wonders whether these herbs have some inherent properties to cure a variety of the aliments or a role other than their therapeutic action.

Some modern Ayurvedic practitioners have tried to explain the scientific basis of the use of these herbals. According to Dutt and King (Dutt, U. C. and King, G. Materia Medica of Hindus Calcutta, 1900) these herbals are added to the formulations often without reason or sometime only for the sake of rhyme. Lakshmipathi (Lakshmipathi, A., One Hundred Useful Drugs, 3rd edn., Arogya Ashram Samithi, Madras, 1946) reported that these herbals are useful in correcting the balance of Kapha, Vata and Pitta which are according to Ayurvedic experts, the three humors of the body, the imbalance of which is responsible for the diseased state. Bose (Bose, K. G., Pharmacopoeia Indica, Bose Laboratories, Calcutta, India 1928) makes a positive mention of the property of long pepper for increasing efficacy of Vasaka as antiasthmatic.

We have studied in detail the Scientific basis for the extensive use of these herbals belonging to Trikatu group. We, in our earlier report (Usha Zutshi and J. L. Koul, Indian Drugs, 19 (12), 476–479, 1982), observed the effect of Trikatu as a whole on vasicine resulting in enhanced bioavailability (and therefore the activity) of this drug to a great extent. *Piper longum* and *Piper nigrum* both are almost equally effective whereas singer (*Zingiber officinalis*) alone has no significant such enhancing effect (FIG. 1 and FIG. 2 of the drawing accompanying this specification.

On our further studies on the above subject, we have now found that piperine, the active principle of the Piper species, is responsible for increase in the bioavailability of the drugs in blood and thereby enhancing the efficacy of the drug.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

Figure 1:
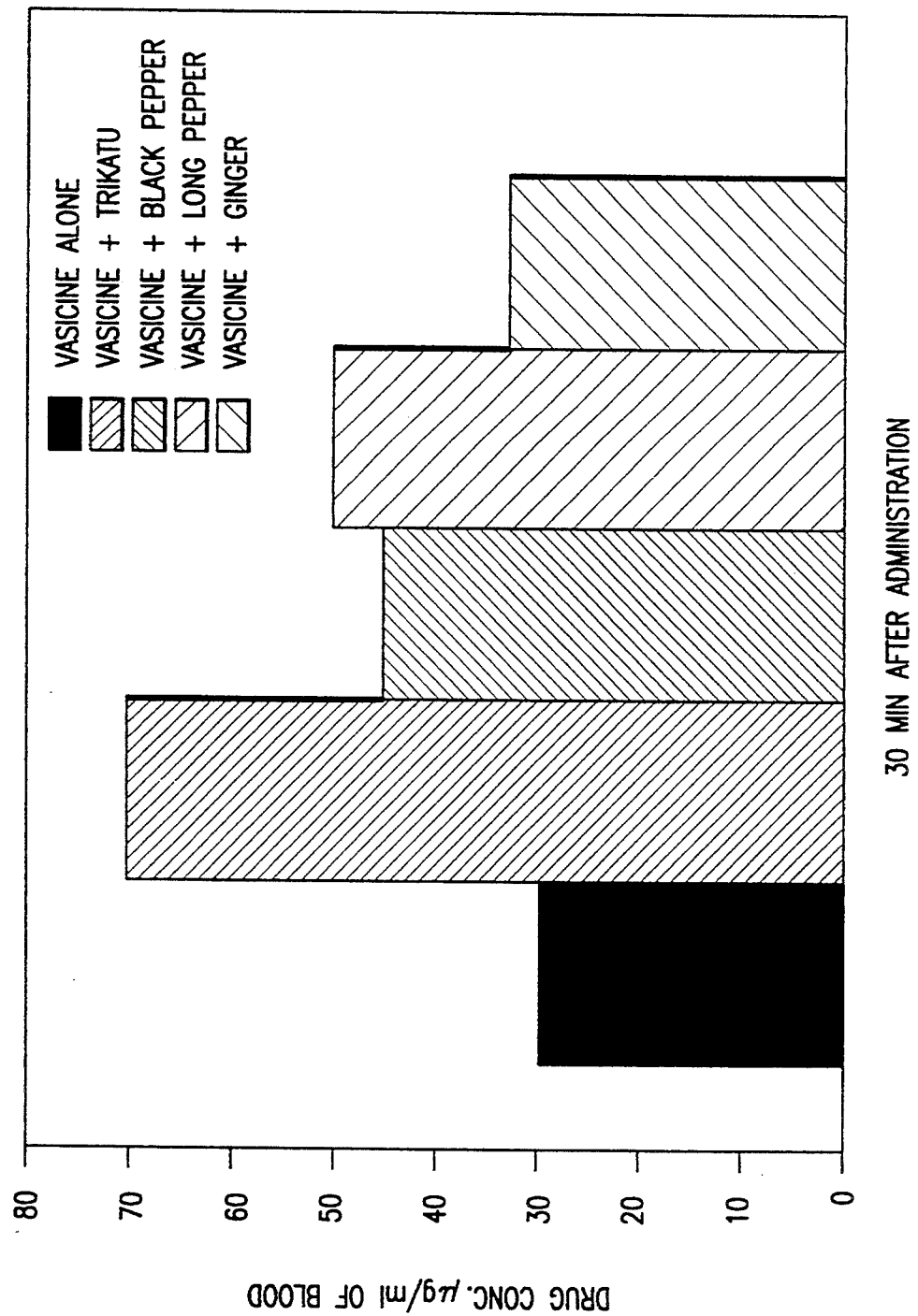
FIG. 1 depicts the drug concentration in the blood thirty minutes after administration of various components administered in association with a vaccine.
Figure 2:
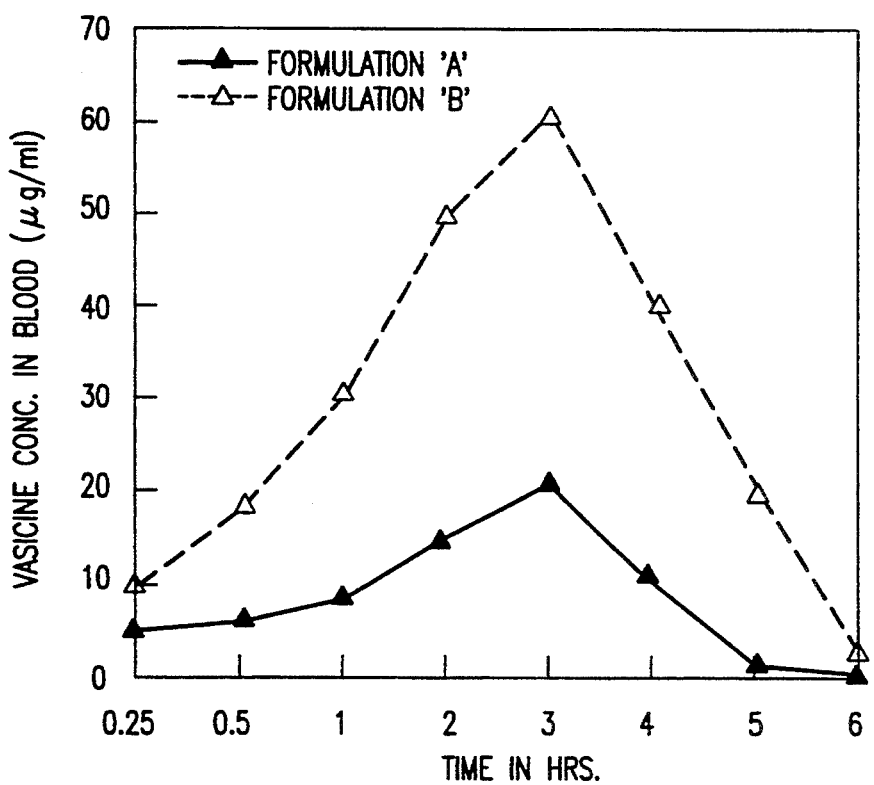
FIG. 2 depicts the relationship between the vaccine concentration in blood and the time after vaccine administration.

Piperine, (E, E) 1-[5-(1,3-benzodioxyl-5-yl)-1-oxo-2,4-pentadenyl] piperidine, of the formula

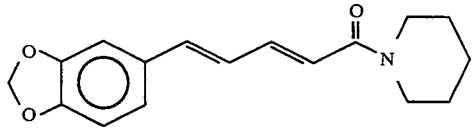

of the drawings accompanying this specification is the main constituent of many Piper species. It is mostly obtained from *Piper longum* (3–5%) or *Piper nigrum* (3–9%) which are cultivated commercially.

Piperine forms monoclinic prisms from ethanol mp 130° C. It is tasteless at first but induces a burning sensation after a few seconds. It is neutral to litmus (pKa 12.22). It is soluble in benzene, chlorform, ether, ethyl acetate, dichloromethane, alcohol, acetic acid and insoluble in water, pet. ether.

On alkaline hydrolysis it furnishes a base piperidine and the acid viz. piperic acid, mp 216° C. It may be synthesized by condensing the two components under proper conditions.

UV (methanol): max 340 mu (32,000).

IR (KBr): 1633, 1610, 1580, 1510, 1440, 1250, 1190, 1130, 1030, 995, 930, 842 cm−1.

13 C NMR (CDCl3): 130.0 (C-1), 107.5 (C-2), 147.0 (C-3), 147.0 (C-4), 105.0 (C-5), 121.5 (C-7), 137.0 (C-8), 141.0 (C-9), 119.5 (C-10), 168.0 (C-11), 44.1 (C-1), 25.3 (C-2'), 24.0 (C-3' 25.3 (C-4') 44.1 (C-5'), 100.4 (C-6').

1H NMR (CDCl3): 1.60 (6H, bs, 3×CH2, 3.53 (4s, bs, 2×NCH2), 5.96 (2H, s, O—CH2—O—), 6.42 (d, j=15Hz,—CH=C), 6.72-7.86 (4H, m, olefinic & Ar-H), 6.90 (1H, d, J=9Hz, Ar-H) 7.25-7.51 (1H, m,

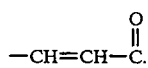

MS (%): M+ 285 (13.6), 200 (100), 172 (42.5), 142 (31.0), 114 (75.1), 84 (32.5).

Piperine can be isolated from oleo-resin of *Piper nigrum* (Black pepper) or *Piper longum* (Long pepper). The powdered fruits of the plant (*Piper nigrum*) are extracted with dichloromethane at room temperature with stirring for 12 hours. The extract is filtered, concentrated in vacuum and the residue is subjected to purification on an alumina column. Pure piperine can be obtained either from petroleum ether/ethyl acetate fractions or dichloromethane to give crude piperine. Pure piperine can be obtained by crystallisation from ethanol. Piperine can also be obtained directly from the crude residue in lesser amounts by extraction in alcohol, filtration and successive crystallisation.

The urine steroid profiles almost always contain the metabolic compounds of the formula 2 to 5 (FIG. 3) of piperine which enter the body through pepper consumed with the food. The metabolites of the formulae 2 and 3 are lacking in 10% individuals. Instead, these persons excrete the precursors having the formula 4 and 5 shown in FIG. 3.

The bioavailability studies with rifampicin and other antituberculosis or anti-leprosy drugs in combination with piperine have, in fact, been very critically examined by us. The formulation containing rifampicin and other antituberculosis/leprosy drugs and piperine in a predetermined dose has been further subjected to a detailed study with respect to its toxicity profile, general pharmacology and shelf life stability. This has been done in view of the importance of these drugs in the treatment of two of the most dreaded diseases i.e. tuberculosis and leprosy.

The above mentioned studies conducted by use reveal that rifampicin and other anti-tuberculosis drugs when combined with piperine have always resulted in significantly increasing the bioavailability of these drugs.

We have also observed that the synergistic activity of piperine on drugs is not uniform and appears to be selective. This is based on our finding that piperine has no effect of enhancing the bioavailability of synthetic anti-diabetic drugs such as tolbutamide.

Figure 3:
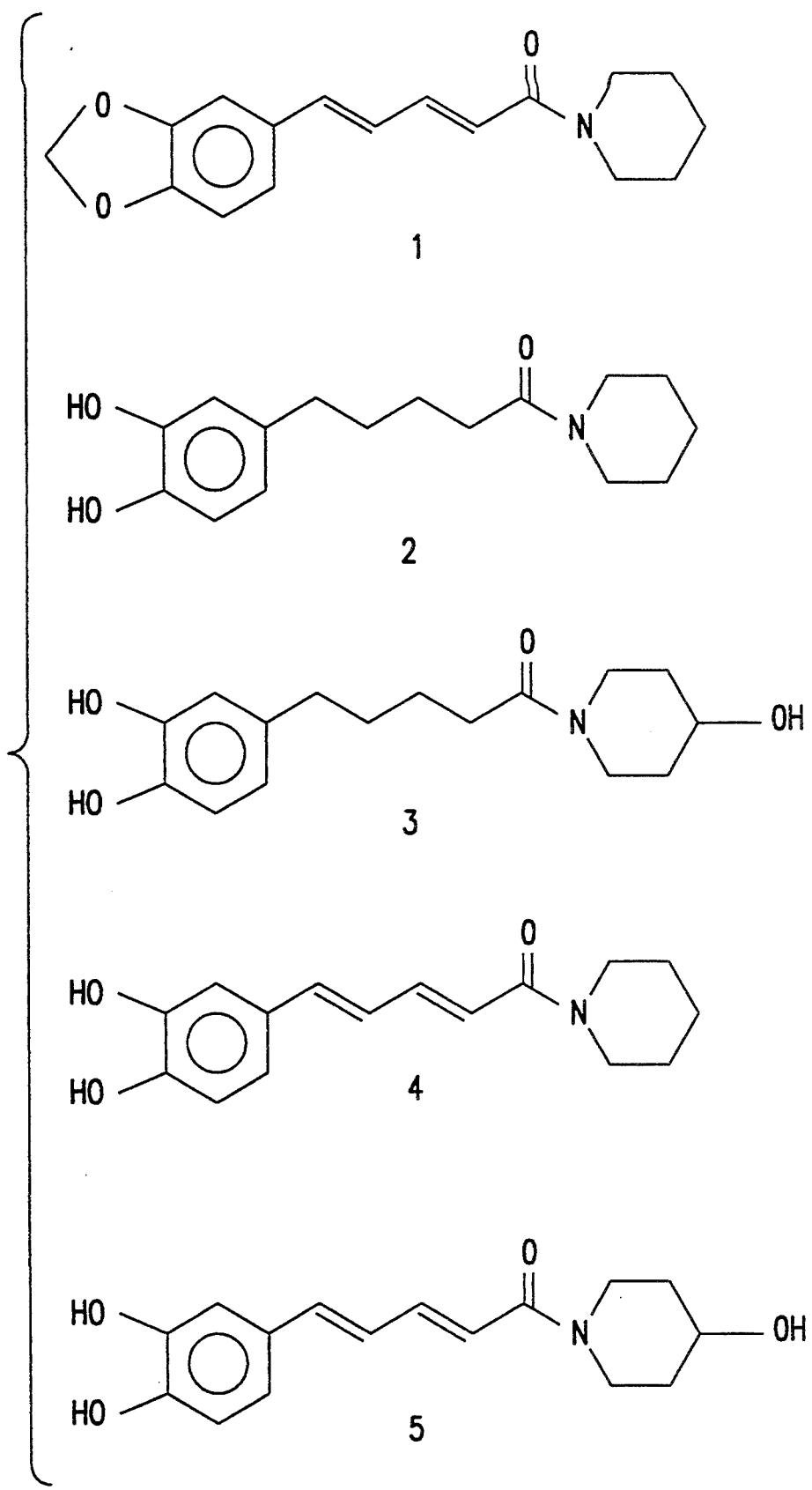
FIG. 3 depicts the structures of piperine and various derivatives.

According to the present invention, there is provided a pharmaceutical composition for the piperine of the formula 1 shown in FIG. 3 of the drawing accompanying this specification with known antituberculosis or antileprosy drugs or the mixtures thereof.

In a preferred embodiment of the invention the quantity of piperine may range from 0.4 to 0.9% by wt. of the antituberculosis or antileprosy drugs. The antituberculosis/leprosy drugs may be selected from rifampicin, isoniazid, pyraziamide, ethambutol, dapsone and the like. The incorporation of piperine with anti-tuberculosis or leprosy drug results in a synergistic composition having unexpected increased bioavailability of the said drugs. Therefore, the invention does not involve simple mixing of the components. It is also to be noted that the piperine has no pharmacological properties but whe mixed with the anti-tuberculosis/leprosy drugs forms a synergistic effect on the said drugs resulting in the enhanced activity of the drug.

All the three antituberculosis drugs viz. isonized, pyrazinamide and rifampicin in combination with piperine showed significant increase in their plasma levels (in rats). This resulted in very high AUC compared to that obtained with the drugs when administered without piperine in equivalent doses. Based on these results, the combination of these three drugs with piperine as shown in Formulation A and Formulation B (indicated below) in predetermined doses was evaluated.

parative plasma levels at 2 h were 11.0±1.0 μg/ml whereas the peak (17.65±1.09 μg/ml) was attained at 4 h. Levels at 24 h interval were found to be again higher (2.5±0.11 μg/ml). The plasma levels with a dose of 450 mg of drug in formulation B were further found to be higher at any time interval than those reported rimactane (trade mark of Ciba-Geigy for rifampicin). A significant decrease in absorption half-life and increase in elimination half-life for the drug in formulation B of the invention was also observed (Table 1).

Pyrazinamide levels in plasma (FIG. 6) with formulation A showed peak of 27.0±2.0 μg/ml at 4 h. By 24 h interval the levels cam down to 1.9±0.25 μg/ml. The comparative levels and peak concentration of the drug with formulation B were certainly higher being 30.0±2.0 μg/ml at 2 h and the peak of 40.0±1.54 μg/ml by 4 and 5.0±0.40 μg/ml by 24th. A highly significant decrease in absorption half-life and increase in elimination half-life for the drug in formulation B was also observed (Table 1).

TABLE 1

| Kinetic Parameter | influence of Piperine on pharmacokinetics of rifampicin, isoniazid and pyrazinamide combination in human volunteers. | | | | | |
|---|---|---|---|---|---|---|
| | Formulation 'A' | | | Formulation 'B' | | |
| | Rifampicin | Isoniazid | Pyrazinamide | Rifampicin | Isoniazid | Pyrazinamide |
| $T\,ab_{0.5}(h)$ | 0.67 ± 0.008 | 0.64 ± 0.01 | 0.60 ± 0.03 | 0.40 ± 0.04** | 0.42 ± 0.04** | 0.37 ± 0.008** |
| $T\,eli_{0.5}(h)$ | 8.40 ± 0.06 | 7.90 ± 0.10 | 9.50 ± 0.14 | 11.1 ± 0.18** | 8.15 ± 0.26* | 11.0 ± 0.17** |
| $c_{max}(pg/ml)$ | 8.20 ± 0.46 | 2.56 ± 0.17 | 27.0 ± 2.0 | 17.6 ± 1.09** | 10.07 ± 0.90** | 40.0 ± 1.64** |
| $AUC^{o-a}\,pg/ml/h)$ | 104.6 ± 4.38 | 41.0 ± 1.72 | 318.6 ± 8.05 | 143.95 ± 5.85** | 94.95 ± 3.98** | 435.41 ± 9.7** |

\* = Not significant (P > 0.05),
\*\* = Highly significant (P < 0.001)

Drug Combination

| Drug | Formulation 'A' | Formulation B |
|---|---|---|
| Isoniazid | 300 mg | 300 mg |
| Pyrazinamide | 1500 mg | 1500 mg |
| Rifampicin | 450 mg | 450 mg |
| Piperine | nil | 20 mg |
| Experimental Design | | |
| Subject | 7M + 7F | |
| Age | 25 to 40 Yrs. | |
| Weight | 40 to 62 kg | |

All subjects were non-smokers and kept off other medication of alcohol for at least 10 days prior to the initiation of the study. All served as self controls were given a uniform diet throughout the study. A 10 days wash out period was given between the administration of formulation A and B.

Pharmacokinetic Analysis

Figure 4:
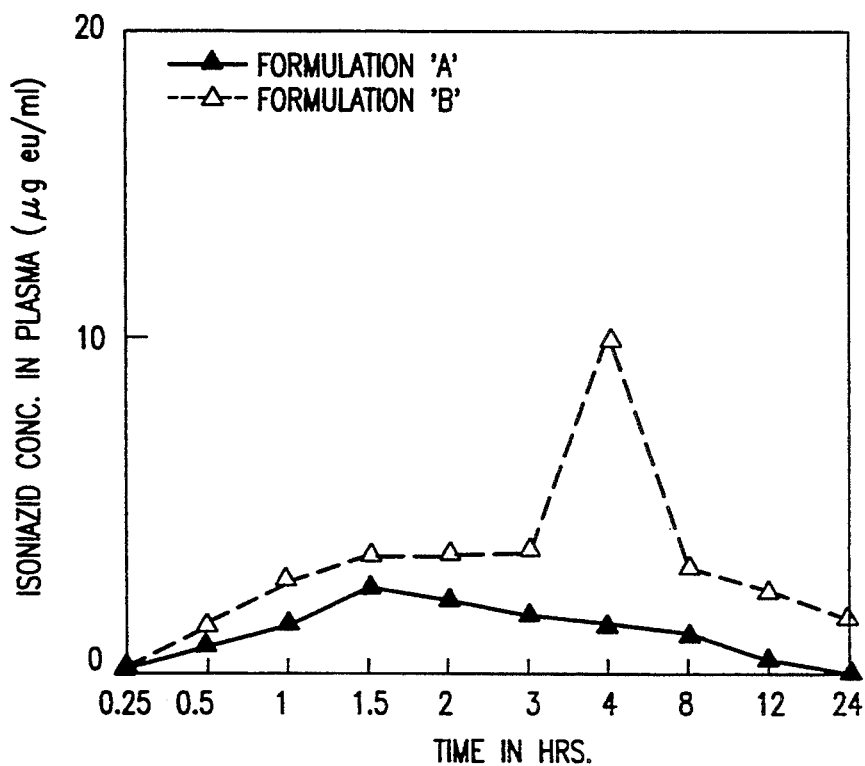
FIG. 4 depicts the relationship between the concentration of isoniazid in plasma and the time after administration for formulations A and B.
Figure 5:
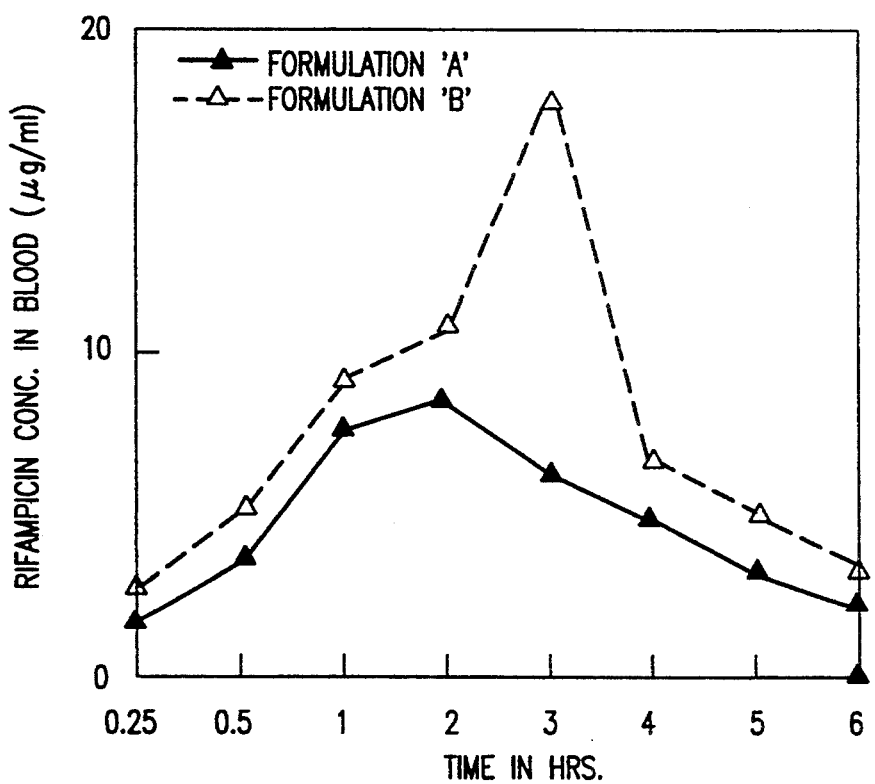
FIG. 5 depicts the relationship between the concentration of rifampicin in blood and the time after administration for formulations A and B.
Figure 6:
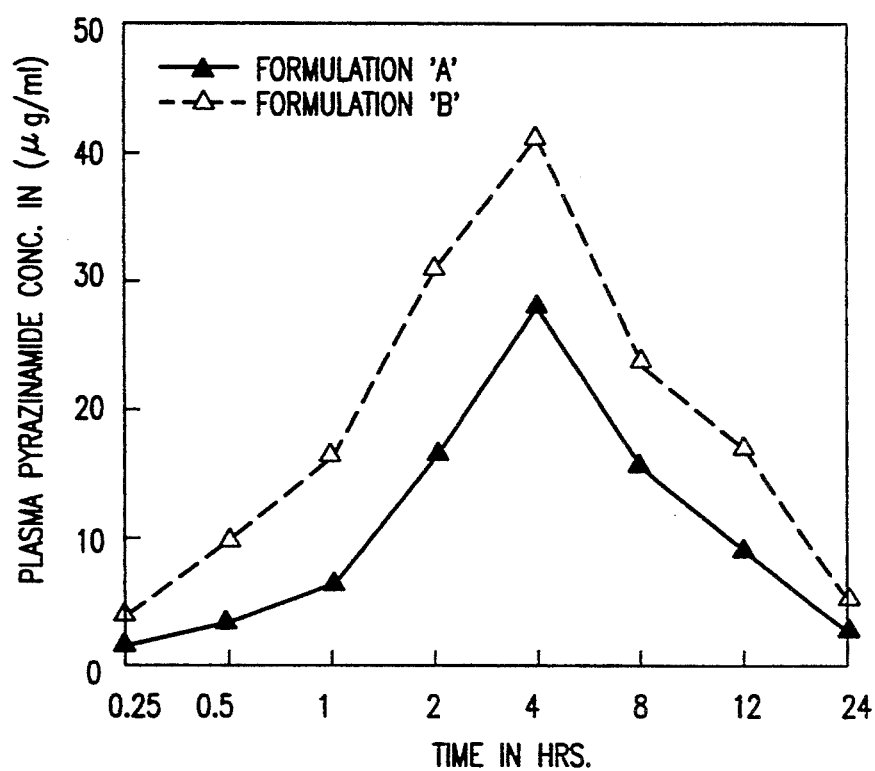
FIG. 6 depicts the relationship between the concentration of pyrazinamide in plasma and time after administration for formulations A and B.
Figure 7:
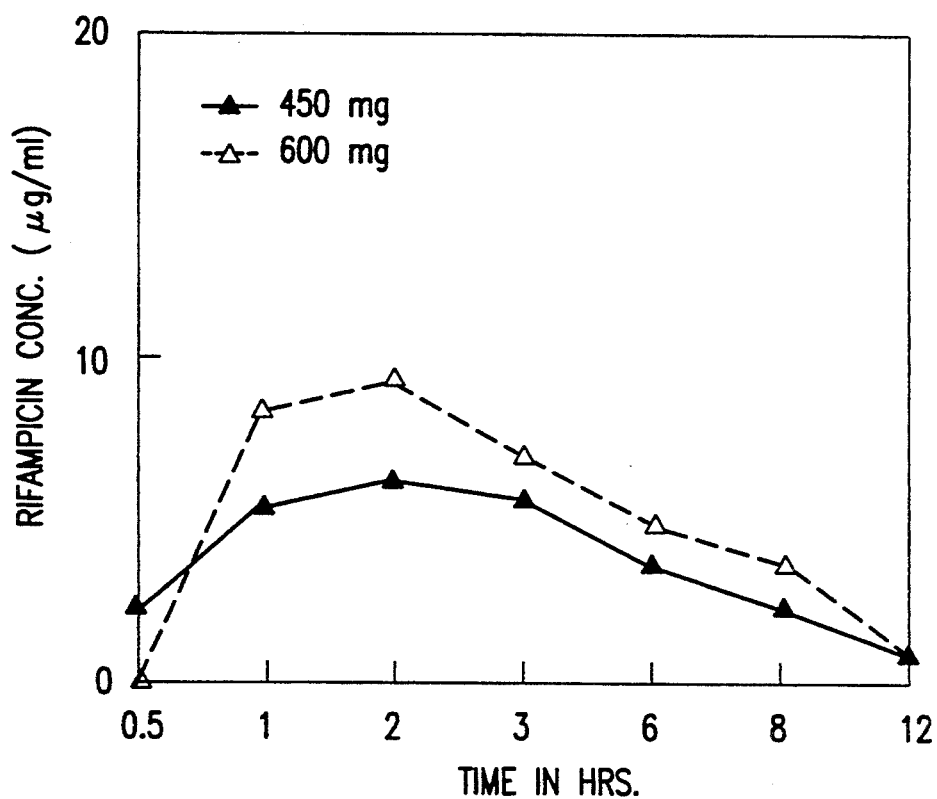
FIG. 7 depicts the relationship between the concentration of rifampicin and the time after administration.
Figure 8:
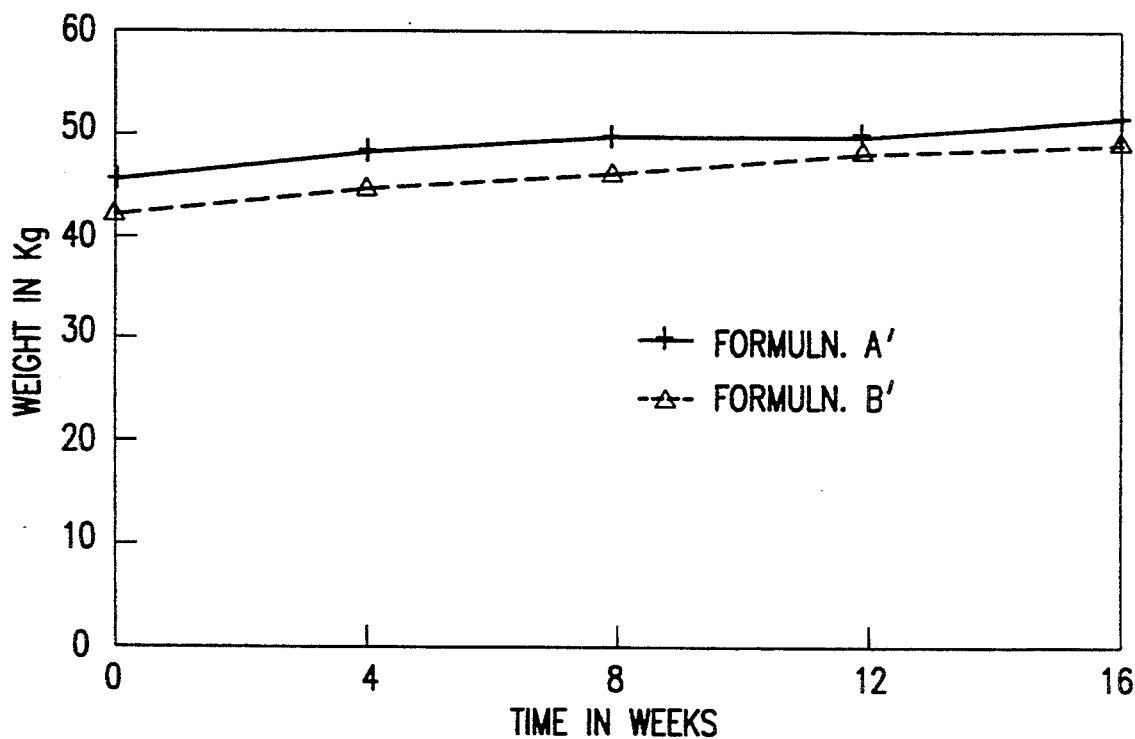
FIG. 8 depicts the relationship between the mean weight in kilograms and the time in weeks after administration.

Kinetic parameters and drug levels in plasma with formulation A abd B are presented in table 1 and FIGS. 4,5 and 6. Peak plasma levels of isoniazed are shown in FIG. 4 in formulation A to be 2.56±0.17 μg/ml by 1 hr with imperceptible levels at 24 hr sampling. In respect of formulation B, the plasma level of the drug at 1 h is 3.1+0.01 μg/ml but peak level is reached by 4 h—to be 10.07+0.09 μg/ml. Further, even at post administration-interval of 14 hr, the plasma levels are comparatively higher & well perceptible (1.70+0.08 μg/ml). Absorption half-life in formulation B is significantly decreased though elimination half-life is almost unchanged compared to formulation A (Table 1).

Rifampicin levels with formulation A (FIG. 5) showed peak plasma levels of 8.2±μg/ml at 2 hr. By 24 h post administration interval the level fell to 1.9±0.1 μg/ml. On the other hand, with formulation B the com- Similarly, rifampicin (also used in the treatment of leprosy, alone in combination with piperine produces the same pharmacokinetic results as that in the drug combination of rifampicin, isoniazid, pyrazinamide and piperine given above. Therefore, this application also confirms and covers the usefulness of the combination of piperine wth rifampicin in the treatment of leporsy.

Enhanced plasma levels & elimination half-lives and decreased absorption half-lives of all the above said three drugs studied reveal an extraordinary information that the calculated reduced dose of these drugs in presence of piperine would produce a therapeutic efficacy equivalent to that of the formulation containing higher doses of same drugs without piperine.

Based on the above pharmacokinetic results, different compositions of the drugs mentioned below in the appropriate amount shown is mixed with piperine in an amount indicated for the treatment of tuberculosis and/or leprosy, have been formulated.

| | Antituberculosis combination |
|---|---|
| Ethambutol | 8 to 18 mg/kg. of body weight |
| Rifampicin | 100 to 300 mg |
| Isoniazid | 100 to 300 mg |
| Pyrazinamide | 500 to 1000 mg |
| Piperine | 5 to 20 mg |

By way of illustration of the invention described above, we have formulated the following the two formulations and have carried out detailed study on tuberculosis patents.

By way of illustrating the invention we have prepared the following two formulations containing different antituberculosis drugs than those described earlier in this specification.

| Drugs | Formulation A | Formulation B |
|---|---|---|
| Refampicin | 450 mg | 200 mg |
| Isoniazid | 300 mg | 300 mg |
| Ethambutol | 15–20 mg/kg | 15 mg/kg |
| Piperine | Nil | 10 mg |

The Formulations were evaluated in patents of pulmonary tuberculosis under Drug Control Authority of Govt. of India approved Phase II clinical trial at Chest Diseases Hospital, Govt. Medical Colleges, Jammu according to an Area Ethic Committee approved protocol. The concentrations of isoniazid and ethambutol were kept constant in both the formulations so as to verify that efficacy of reduced dose of rifampicin. However, the enhanced plasma levels of isonazid and ethambutol (given below under drug plasma levels) warrant a reduction in their doses.

Based on the quantities of various drugs given above any antituberculosis combination containing two or more drugs and piperine can be formulated to possess the requisite therapeutic efficacy.

Data Analysis

The data obtained during evaluation of formulations A' and B' is described with particular reference to the following therapeutic efficacy markers:
Drug plasma levels
Radiological response
Weight record
(ESR) Erythrocyte Sedimention Rate response

Drug Plasma Levels

It is interesting and scientifically therapeutically significant that for rifampicin Cmax value of $10+20\pm1.20$ $\mu g/ml$ with formulation B'0 is higher (though marginally) then that of formulation A' ($8.60+0.70$ $\mu g/ml$) inspite of the fact that the amount of rifampicin in formulation B stands at less than half plasma levels of other two drugs viz. is isoniazed and ethambutol stand significantly enhanced as given below:

|  | Formulation A | Formulation B |
|---|---|---|
| Isoniazed | 4.20 + 0.76 | 8.21 + 1.10 |
| Ethambutol | 3.60 + 0.58 | 6.40 + 0.89 |

Figure 10:
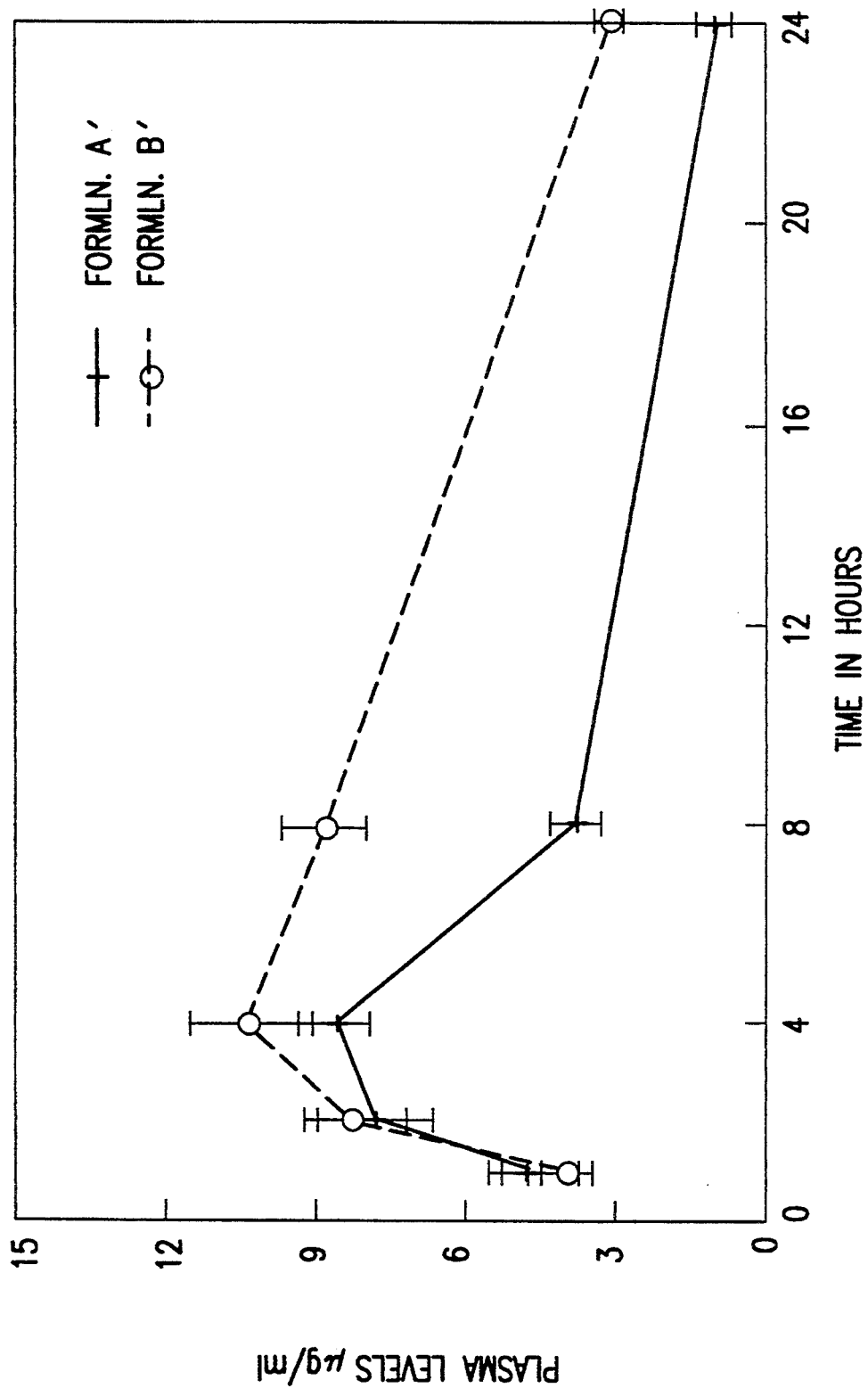
FIG. 10 depicts the relationship between rifampicin plasma levels and time (short-term) after administration in patients.
Figure 11:
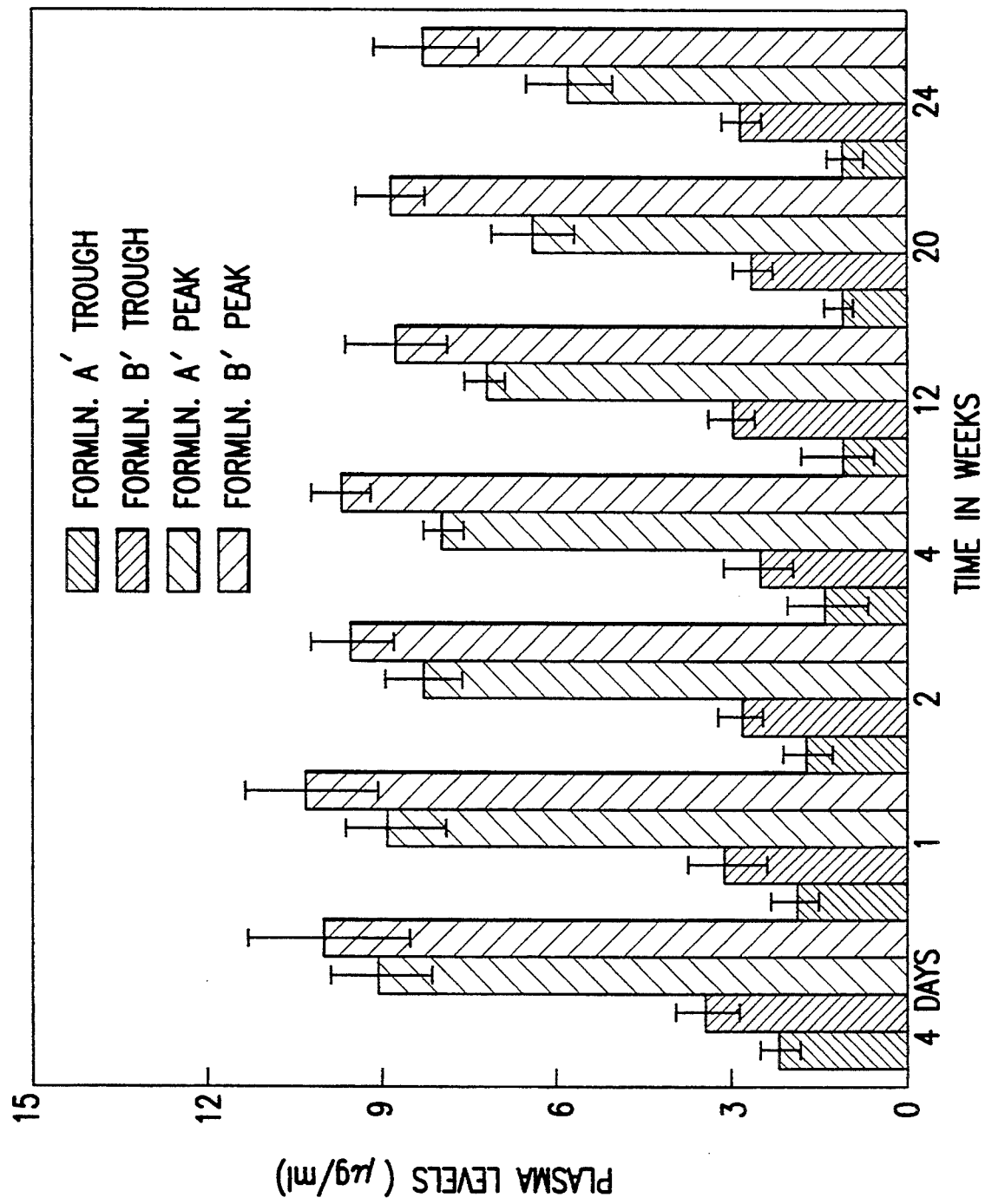
FIG. 11 denotes the relationship between rifampicin plasma levels and time (long-term) after administration in patients.
Figure 12:
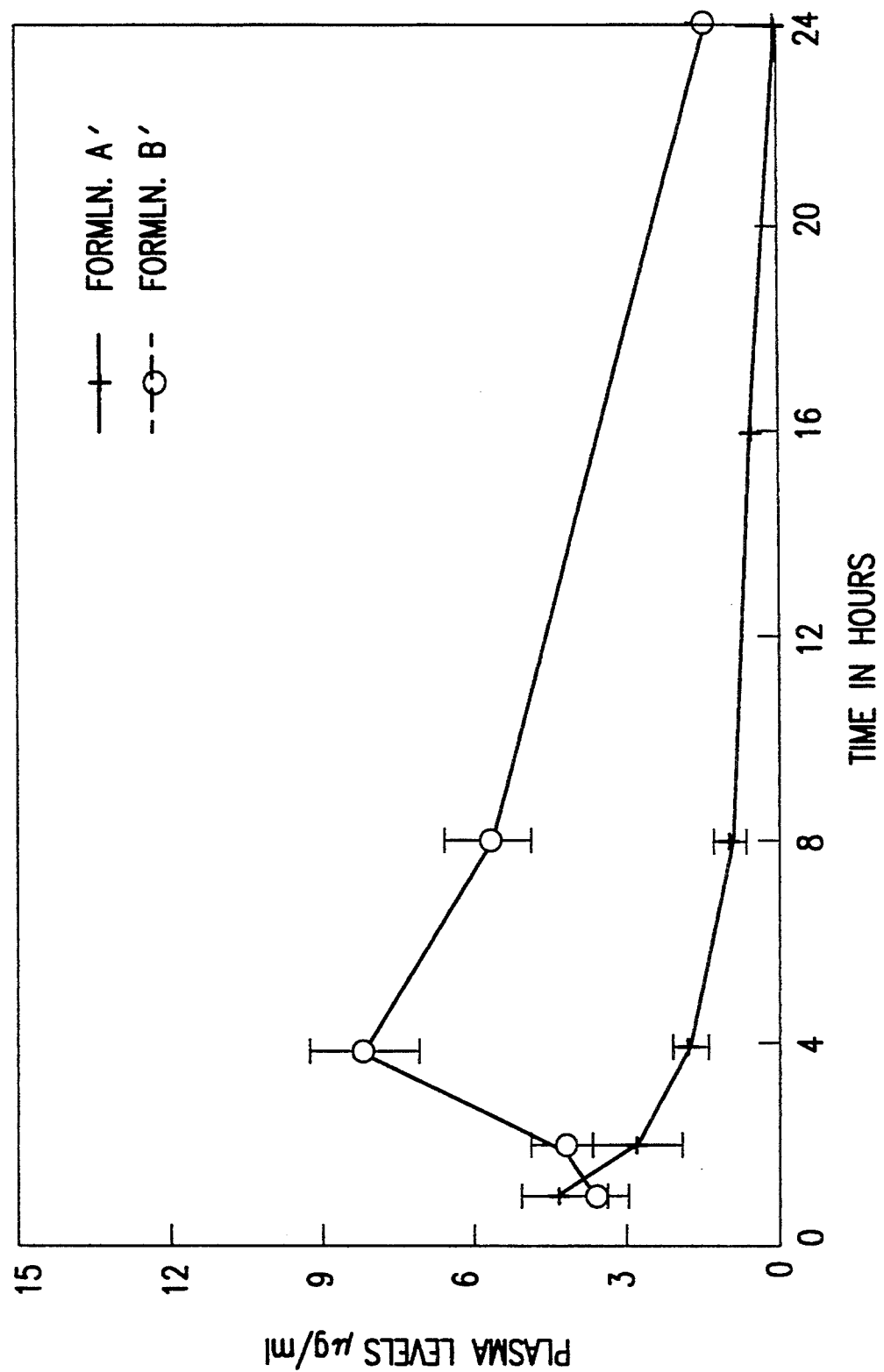
FIG. 12 depicts the relationship between isoniazid plasma levels and time (short-term) after administration in patients.
Figure 13:
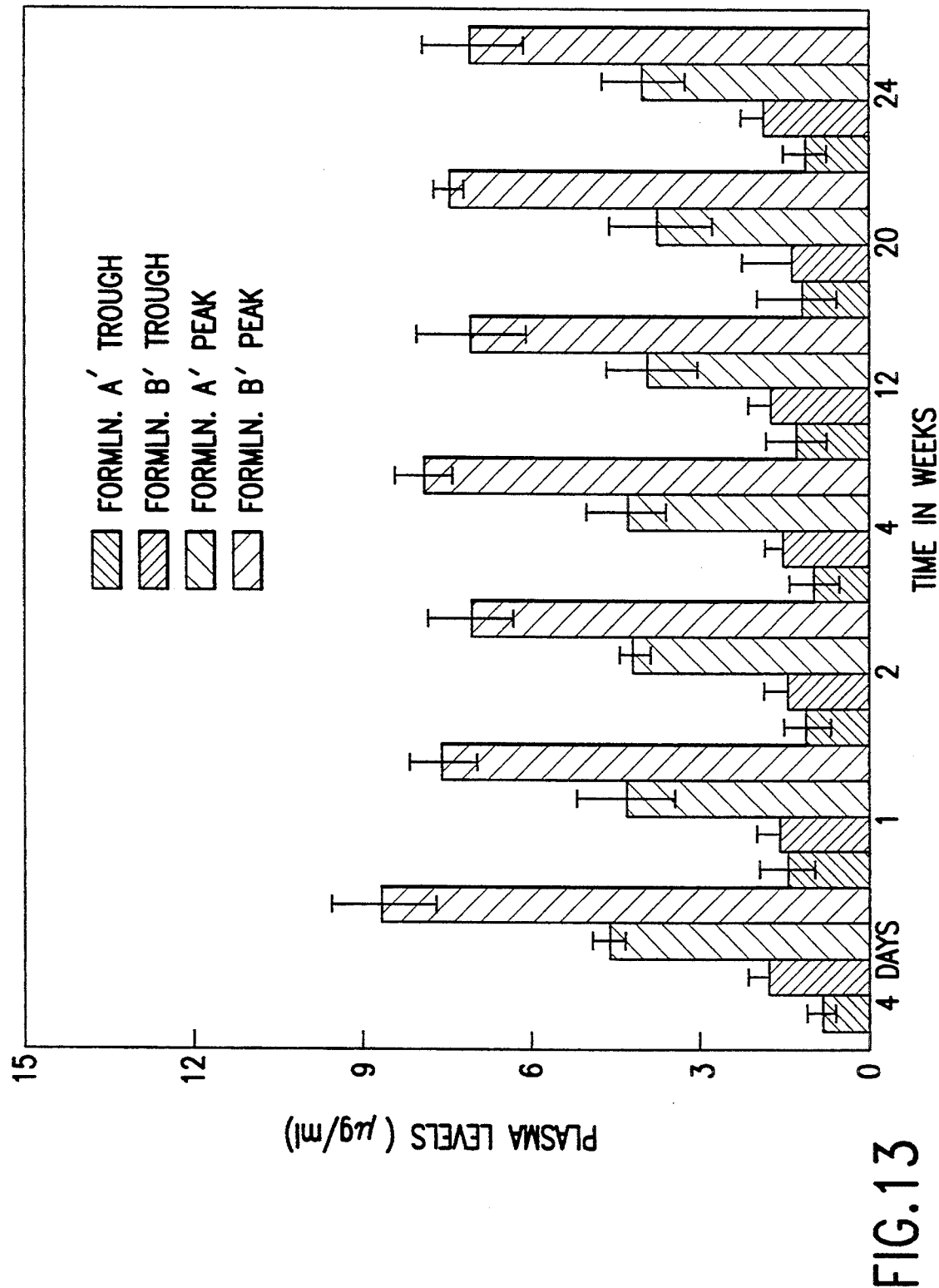
FIG. 13 depicts the relationship beteen isoniazid plasma levels and time (long-term) after administration in patients.
Figure 14:
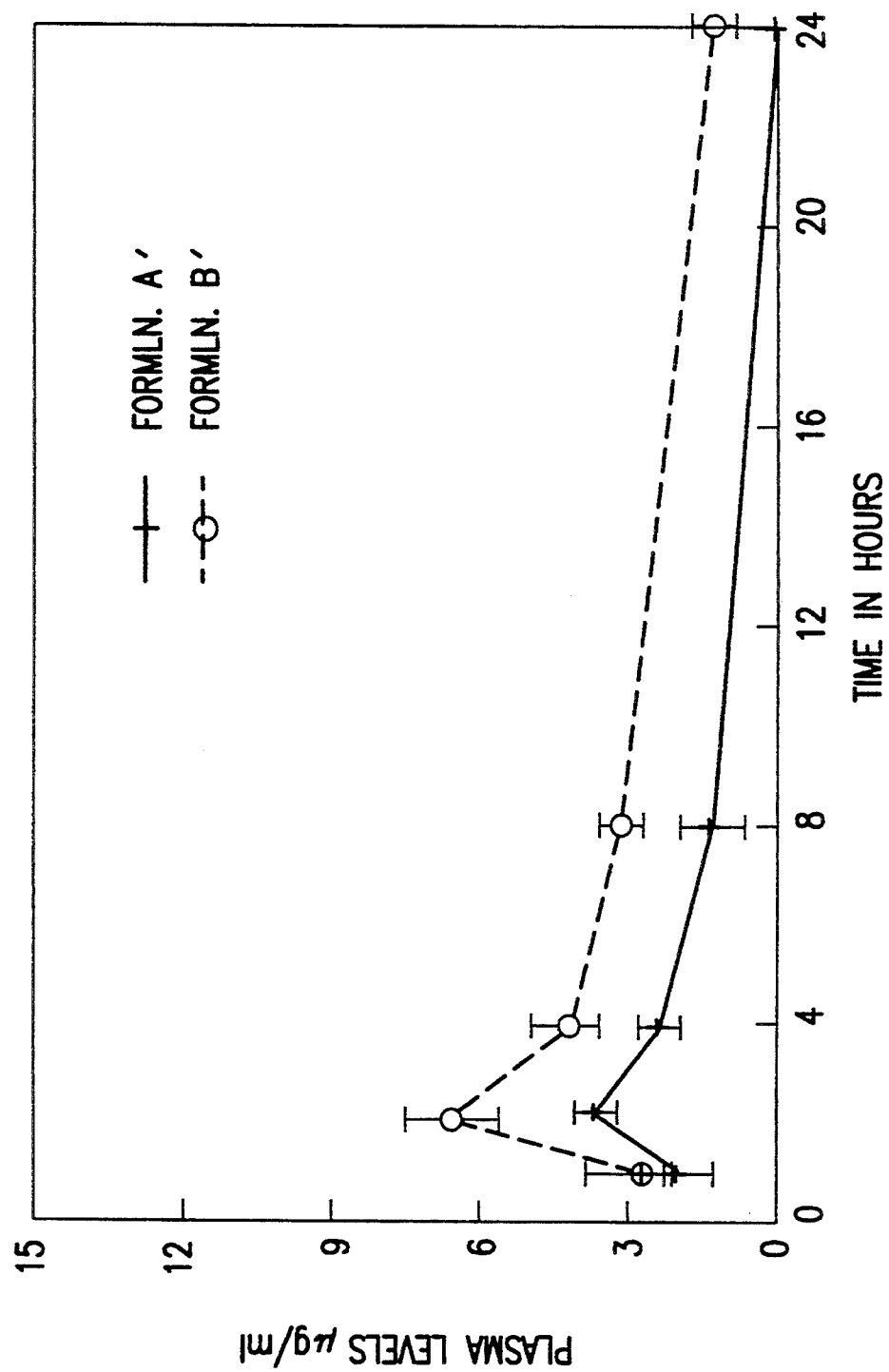
FIG. 14 denotes the relationship between ethambutol plasma levels and time (short-term) after administration in patients.
Figure 15:
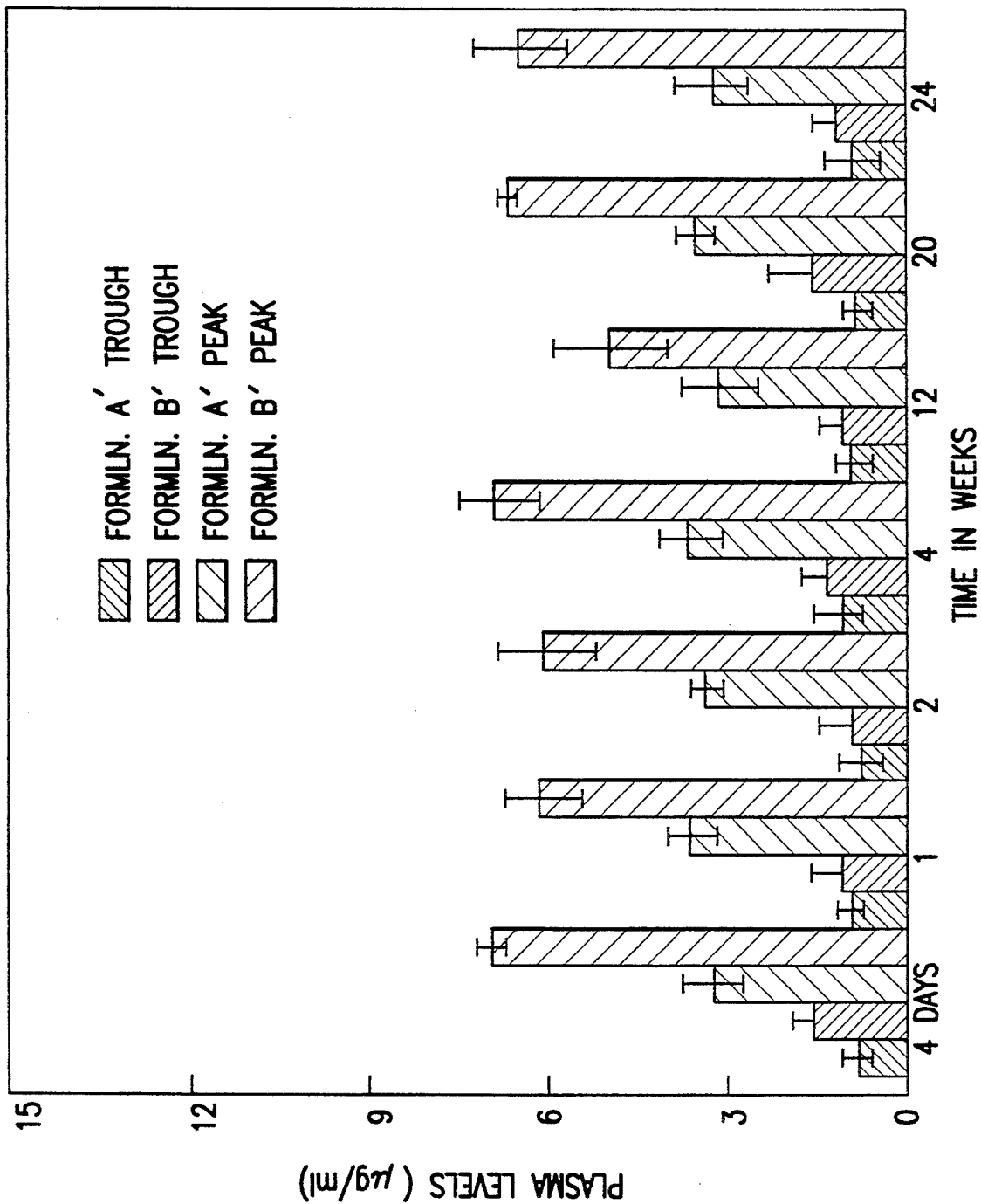
FIG. 15 depicts the relationship between ethambutol plasma levels and time (long-term) after administration in patients.

The peak plasma levels of all the three drugs on day 1 of commencement of Anti Tuberculosis Therapy (ATT) are presented in FIGS. 10, 12 and 14. The steady state levels for all the three drugs from day 4 of commencement of ATT are presented in FIGS. 11, 13, and 15 and Table 4.

As is clear from the figures through and peak levels of all these drugs are visibly higher in formulation containing piperine (A) as compared to formulation (A) without piperine. But the significant part of steady state levels of rifampicin is the comparatively very slow fall in its levels over a period of 24 weeks in patients treated with formulation B. It could be possibly due to the reason that piperine has inhibiting effect on enzyme induction—a phenomenon well known to cause progressive increased elimination of rifampicin in prolonged therapy.

Radilogical response

At the end of 12 weeks ATT, Group B had an equal percentage of '+' (one plus) score patients when compared with group A (Tables 2 and 3). The clinical finding is highly significant by virtue of following facts:
1. Reduced dose of rifampicin in formulation (Group) B' as compared to formulation A'.
2. Highest number of patients with 4+ disease (extensive, bilateral with carities) in Group B' (11 patients) compared to Group A' (6 patients).

Weight record

The find weight gain is almost identical in both the formulations and 6 legs for formulation B' (FIG. B).

ESR

Figure 9:
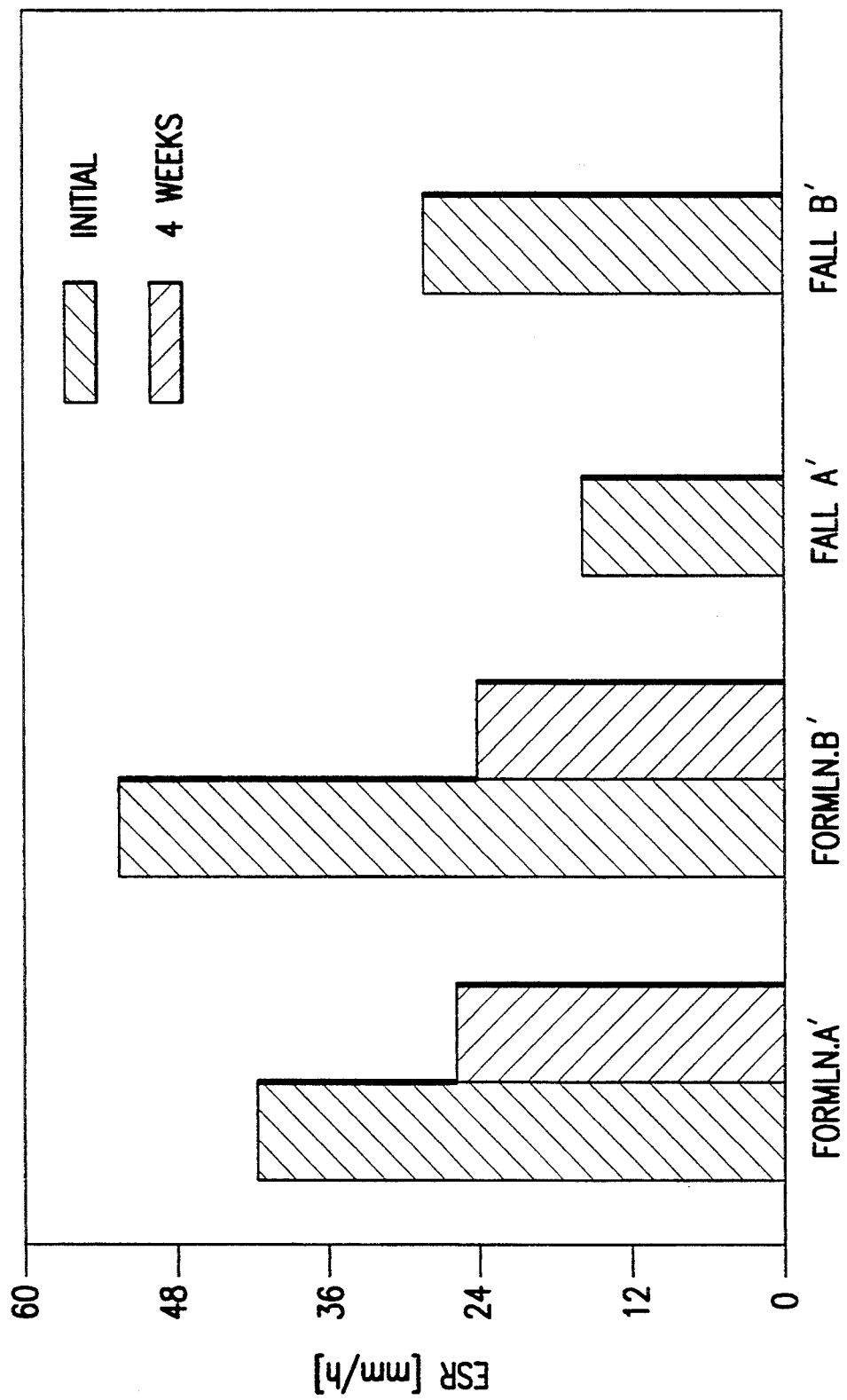
FIG. 9 depicts the mean ESR values initially and four weeks after administration for various formulations.

ESR showed significantly greater reduction in Group B' than in Group A' indicating favourable response to the therapy and more than confirming the therapeutic equivalence (rather superiority) of formulation B' to that of formulation A' (FIG. 9).

Based on above data, the reduction in doses of isoniazid, ethambutol and pyrazinamide have been calculated. Drug Control Authority of India have cleared these formulations for phase III clinical trails in patients of pulmonary tuberculosis.

Rifampicin is a drug common to ATT and Anti-Leprosy Therapy (ALT). Because of the increased therapeutic efficacy of reduced doses of rifampicin in presence of piperine proven by out studies in tuberculosis patinets, it leaves no doubt that the same should apply to ALT in combination with other anti-leprosy drugs.

On the above basis the under mentioned formulation has been prepared.

|  | Anti-leprosy combination |
|---|---|
| Rifampicin | 100 to 300 mg |
| Piperine | 5 to 20 mg |

In a similar manner any other anti-leprosy drugs may be mixed with piperine.

The examples of formulation both anti-tuberculosis as well as anti-leprosy given above should not be construed so as to limit the scope of this invention. In fact, following these examples, any suitable and desired pharmaceutical formulation for the treatment of leprosy and tuberculosis can be prepared. The composition of the invention can be in any form commonly employed for administration such as tablets, capsules, injectables and the like.

TABLE 2

DISEASE SCORE [INITIAL AND AFTER TREATMENT] WITH FORMULATION A'

| INITIAL SCORE | No. OF PATIENTS | TREATMENT DURATION IN WEEKS | | | | | |
|---|---|---|---|---|---|---|---|
| | | 4 | | 12 | | 24 | |
| | | S P | (%) | P | (%) | P | (%) |
| ++++ | 6 | 4+ 1 | (17) | NIL | | NIL | |
| | | 3+ 3 | (50) | 3 | (50) | NIL | |
| | | 2+ 2 | (33) | 1 | (17) | NIL | |
| | | 1+ NIL | | 2 | (33) | 2 | (33) |
| | | 0 NIL | | NIL | | 3 | (50) |
| | | | | | | 1 Pt. X-RAY ON NEXT VISIT | |
| +++ | 7 | 4+ NIL | | NIL | | NIL | |
| | | 3+ 3 | (43) | NIL | | NIL | |
| | | 2+ 3 | (43) | 3 | (43) | NIL | |

TABLE 2-continued
DISEASE SCORE [INITIAL AND AFTER TREATMENT] WITH FORMULATION A'

| INITIAL SCORE | No. OF PATIENTS | TREATMENT DURATION IN WEEKS | | | | | |
|---|---|---|---|---|---|---|---|
| | | 4 | | 12 | | 24 | |
| | | S | P (%) | P (%) | | P (%) | |
| | | 1+ | 1 (14) | 3 (43) | | NIL | |
| | | 0 | NIL | 1 (14) | | 2 (28) | |
| | | | | | | 5 Pt. X-RAY ON NEXT VISIT | |
| ++ | 1 | 4+ | NIL | NIL | | NIL | |
| | | 3+ | NIL | NIL | | NIL | |
| | | 2+ | NIL | NIL | | NIL | |
| | | 1+ | 1 (100) | 1 (100) | | NIL | |
| | | 0 | NIL | NIL | | 1 (100) | |
| + | 1 | 4+ | NIL | NIL | | NIL | |
| | | 3+ | NIL | NIL | | NIL | |
| | | 2+ | 1 (100) | NIL | | NIL | |
| | | 1+ | NIL | 1 (100) | | NIL | |
| | | 0 | NIL | NIL | | * | |
| | | | | | | * 24 WEEK X-RAY ON NEXT VISIT | |

S: DISEASE SCORE
P: No. OF PATIENTS
O: HEALED FIBROTIC LESIONS

TABLE 3
DISEASE SCORE [INITIAL AND AFTER TREATMENT] WITH FORMULATION B'

| INITIAL SCORE | No. OF PATIENTS | TREATMENT DURATION IN WEEKS | | | | | |
|---|---|---|---|---|---|---|---|
| | | 4 | | 12 | | 24 | |
| | | S | P (%) | P (%) | | P (%) | |
| ++++ | 11 | 4+ | 2 (18) | NIL | | NIL | |
| | | 3+ | 7 (64) | 4 (36) | | NIL | |
| | | 2+ | 2 (18) | 3 (27) | | 2 (18) | |
| | | 1+ | NIL | 4 (36) | | 1 (09) | |
| | | 0 | NIL | NIL | | 2 (18) | |
| | | | | | | 6 Pt. X-RAYS ON NEXT VISIT | |
| +++ | 3 | 4+ | 1 (33) | NIL | | NIL | |
| | | 3+ | NIL | 1 (33) | | NIL | |
| | | 2+ | 2 (67) | NIL | | 1 (33) | |
| | | 1+ | NIL | 1 (33) | | NIL | |
| | | 0 | NIL | 1 (33) | | 1 (33) | |
| | | | | | | 1 Pt. X-RAY ON NEXT VISIT | |
| ++ | 3 | 4+ | NIL | NIL | | NIL | |
| | | 3+ | NIL | NIL | | NIL | |
| | | 2+ | 2 (67) | NIL | | NIL | |
| | | 1+ | 1 (33) | 3 (100) | | NIL | |
| | | 0 | NIL | NIL | | 2 (67) | |
| | | | | | | 1 Pt. X-RAY ON NEXT VISIT | |

S: DISEASE SCORE
P: No. OF PATIENTS
O: HEALED FIBROTIC LESIONS

TABLE 4
PLASMA LEVELS [ug/ml] IN PATIENTS OF TUBERCULOSIS ORDER TREATMENT-PHASE-II CLINICAL STUDY ON FORMLN. AT-3

| TIME | RIFAMPICIN | | ISONIAZID | | ETHANBUTOL | |
|---|---|---|---|---|---|---|
| | FORMLN. A' | FORMLN. B' | FORMLN. A' | FORMLN. B' | FORMLN. A' | FORMLN. B' |
| DAY 1 | | | | | | |
| 1 h | 4.60 ± 0.87 | 3.90 ± 0.48 | 4.20 ± 0.76 | 3.60 ± 0.670 | 1.90 ± 0.90 | 2.80 ± 0.76 |
| 2 h | 7.80 ± 1.10 | 8.20 ± 0.95 | 2.80 ± 0.84 | 4.20 ± 0.56 | 3.60 ± 0.58 | 6.40 ± 0.89 |
| 4 h | 8.60 ± 0.70 | 10.20 ± 1.20 | 1.70 ± 0.36 | 8.21 ± 1.10 | 2.20 ± 0.43 | 4.20 ± 0.63 |
| 8 h | 3.80 ± 0.48 | 8.80 ± 0.86 | 0.96 ± 0.28 | 5.70 ± 0.77 | 1.20 ± 0.61 | 3.00 ± 0.28 |
| 24 h | 1.10 ± 0.27 | 3.20 ± 0.20 | RN | 1.20 ± 0.44 | RN | 1.10 ± 0.41 |
| 4 DAYS | | | | | | |
| TROUGH | 2.10 ± 0.40 | 3.40 ± 0.56 | 0.85 ± 0.18 | 1.80 ± 0.37 | 0.77 ± 0.24 | 1.60 ± 0.36 |
| PEAK | 9.10 ± 0.90 | 10.00 ± 1.40 | 4.70 ± 0.26 | 8.70 ± 0.90 | 3.30 ± 0.47 | 7.00 ± 0.21 |
| 1 WEEK | | | | | | |
| TROUGH | 1.95 ± 0.25 | 3.10 ± 0.72 | 1.28 ± 0.51 | 1.60 ± 0.43 | 1.00 ± 0.15 | 1.20 ± 0.55 |
| PEAK | 8.90 ± 0.84 | 10.30 ± 1.20 | 4.35 ± 0.88 | 7.70 ± 0.60 | 3.70 ± 0.39 | 6.20 ± 0.71 |
| 2 WEEKS | | | | | | |
| TROUGH | 1.76 ± 0.48 | 2.80 ± 0.54 | 1.16 ± 0.39 | 1.50 ± 0.29 | 0.89 ± 0.32 | 1.00 ± 0.65 |
| PEAK | 8.38 ± 0.65 | 9.66 ± 0.73 | 4.18 ± 0.28 | 7.20 ± 0.71 | 3.55 ± 0.20 | 6.10 ± 0.80 |
| 4 WEEKS | | | | | | |
| TROUGH | 1.40 ± 0.71 | 2.60 ± 0.61 | 0.98 ± 0.46 | 1.55 ± 0.33 | 1.20 ± 0.45 | 1.40 ± 0.49 |
| PEAK | 8.10 ± 0.34 | 9.84 ± 0.53 | 4.34 ± 0.73 | 7.93 ± 0.56 | 3.70 ± 0.51 | 6.90 ± 0.69 |
| 12 WEEKS | | | | | | |
| TROUGH | 1.13 ± 0.69 | 3.00 ± 0.44 | 1.31 ± 0.59 | 1.70 ± 0.40 | 0.93 ± 0.32 | 1.10 ± 0.27 |
| PEAK | 7.30 ± 0.36 | 8.80 ± 0.88 | 3.90 ± 0.81 | 7.10 ± 0.92 | 3.20 ± 0.64 | 6.00 ± 0.20 |
| 20 WEEKS | | | | | | |
| TROUGH | 1.20 ± 0.23 | 2.73 ± 0.34 | 1.20 ± 0.68 | 1.30 ± 0.78 | 0.70 ± 0.19 | 1.60 ± 0.81 |
| PEAK | 6.53 ± 0.61 | 9.00 ± 0.68 | 3.75 ± 0.89 | 7.50 ± 0.18 | 3.56 ± 0.24 | 6.70 ± 0.13 |
| 24 WEEKS | | | | | | |
| TROUGH | 1.00 ± 0.29 | 2.85 ± 0.40 | 1.10 ± 0.35 | 1.80 ± 0.47 | 0.89 ± 049 | 1.30 ± 0.35 |
| PEAK | 5.90 ± 0.76 | 8.36 ± 0.91 | 4.00 ± 0.73 | 7.00 ± 0.95 | 3.30 ± 0.57 | 6.50 ± 0.75 |

RN; NOT MEASURABLE

We claim:

1. A composition for the treatment of tuberculosis and leprosy, having increased therapeutic efficacy, which comprises piperine of the formula

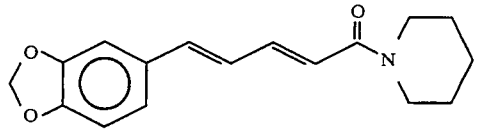

with known antituberculosis or antileprosy drugs or the mixture thereof.

2. A combination as claimed in claim 1, wherein the amount of piperine is in the range of 0.4 to 0.9% by weight of the antituberculosis or antileprosy drugs.

3. A combination as claimed in claim 1, wherein the antituberculosis formulation consists (1) at least two or more of
 (a) Ethambutol: 8 to 15 mg/kg body weight
 (b) Rifampicin: 100–300 mg
 (c) Isoniazid: 100–300 mg and
 (d) Pyrazinamide: 500–1000 mg, and
 (e) Piperine: 5 to 29 mg.

4. A combination as claimed in claim 1, wherein the antileprosy formulation consist of
 Rifampicin: 100–300 mg
 Dapsone: 50–100 mg
 Piperine: 5–20 mg.

* * * * *